(12) United States Patent
Xian et al.

(10) Patent No.: US 9,243,028 B2
(45) Date of Patent: Jan. 26, 2016

(54) FACILE AMIDE FORMATION VIA S-NITROSO THIOACID INTERMEDIATES

(75) Inventors: Ming Xian, Pullman, WA (US); Jia Pan, Jupiter, FL (US)

(73) Assignee: Washington State University, Pullman, WA (US)

( * ) Notice: Subject to any disclaimer, the term of this patent is extended or adjusted under 35 U.S.C. 154(b) by 455 days.

(21) Appl. No.: 13/359,372

(22) Filed: Jan. 26, 2012

(65) Prior Publication Data

US 2012/0190820 A1    Jul. 26, 2012

Related U.S. Application Data

(60) Provisional application No. 61/436,533, filed on Jan. 26, 2011.

(51) Int. Cl.
| | |
|---|---|
| C07C 231/10 | (2006.01) |
| C07D 295/192 | (2006.01) |
| C07K 1/02 | (2006.01) |
| C07C 269/06 | (2006.01) |
| C07C 381/00 | (2006.01) |
| C07D 207/10 | (2006.01) |
| C07D 209/20 | (2006.01) |
| C07D 295/185 | (2006.01) |

(52) U.S. Cl.
CPC ............... *C07K 1/02* (2013.01); *C07C 231/10* (2013.01); *C07C 269/06* (2013.01); *C07C 381/00* (2013.01); *C07D 207/10* (2013.01); *C07D 209/20* (2013.01); *C07D 295/185* (2013.01); *C07D 295/192* (2013.01)

(58) Field of Classification Search
None
See application file for complete search history.

(56) References Cited

FOREIGN PATENT DOCUMENTS

WO    WO 2006/133962    * 12/2006

OTHER PUBLICATIONS

Davarie et al., Organic Letters, 2010, 12(4) 752-754.*
Zhang et al., Organic Letters, 2010, 12(24) 5674-5676.*
Crich et al. Angew Chem. Int. Ed., 2009, 48, 2355-58.*
Al-Sa'Doni, Haitham; Ferro, Albert. (2004). "S-Nitrosothiols as Nitric Oxide-Donors: Chemistry, Biology and Possible Future Therapeutic Applications." *Current Medicinal Chemistry*. vol. 11, No. 20, pp. 2679-2690.
Bode, Jeffrey W. (2006). "Emerging methods in amide- and peptide-bond formation." *Current Opinion in Drug Discovery & Development*. vol. 9, No. 6, pp. 765-775.
Crich, David and Sasaki, Kaname. (2009). "On the Reaction of Thioacids with Isocyanates: A Convenient Amide Ligation Process." *Organic Letters*. vol. 11, No. 15, pp. 3514-3517.
Crich, David and Sharma, Indrajeet. (2009). "Epimerization-Free Block Synthesis of Peptides from Thioacids and Amines with the Sanger and Mukaiyama Reagents." *Angewandte Chemie International Edition*. vol. 48, pp. 2355-2358.
Crich, David and Sharma, Indrajeet. (2009). "Triblock Peptide and Peptide Thioester Synthesis With Reactivity-Differentiated Sulfonamides and Peptidyl Thioacids." *Angewandte Chemie International Edition*. vol. 48, pp. 7591-7594.
Crich, et al. (2007). "Amino Acid and Peptide Synthesis and Functionalization by the Reaction of Thioacids with 2,4-Dinitrobenzenesulfonamides." *Organic Letters*. vol. 9, No. 22, pp. 4423-4426.
Dawson, et al. (1994). "Synthesis of Proteins by Native Chemical Ligation." *Science*. vol. 266, pp. 776-779.
Dawson, et al. (1997). "Modulation of Reactivity in Native Chemical Ligation through the use of Thiol Additives." *Journal of the American Chemical Society*. vol. 119, No. 19, pp. 4325-4329.
Goldstein, Alex S. and Gelb, Michael H. (2000). "An alternate preparation of thioester resin linkers for solid-phase synthesis of peptide C-terminal thioacids." *Tetrahedron Letters*. vol. 41, pp. 2797-2800.
Han, So-Yeop and Kim, Young-Ah. (2004). "Recent development of peptide coupling reagents in organic synthesis." *Tetrahedron*. vol. 60, pp. 2447-2467.
Kimmerlin, T. and Seebach, D. (2005). "'100 years of peptide synthesis': ligation methods for peptide and protein synthesis with applications to β-peptide assemblies." *J. Peptide Res*. vol. 65, pp. 229-260.
Liu, Rihe and Orgel, Leslie E. (1997). "Oxidative acylation using thioacids." *Nature*. vol. 389, pp. 52-54.
Mason, Joan (Banus). (1969). "Trifluoromethyl Thionitrite." *Journal of the Chemical Society A*. pp. 1587-1592.
Nilsson, et al. (2005). "Chemical Synthesis of Proteins." *Annual Review of Biophysics and Biomolecular Structure*. vol. 43, pp. 91-118. (Author Manuscript version submitted herein).
Potapenko, et al. (2004). "Reversible Reactions of Thiols and Thiyl Radicals with Nitrone Spine Traps." *The Journal of Physical Chemistry B*. vol. 108, pp. 9315-9324.
Rao, et al. (2009). "Thio FCMA Intermediates as Strong Acyl Donors: A General Solution to the Formation of Complex Amid Bonds." *Journal of the American Chemical Society (Communications)*. vol. 131, pp. 12924-12926.

(Continued)

*Primary Examiner* — Karlheinz R Skowronek
*Assistant Examiner* — Roy Teller
(74) *Attorney, Agent, or Firm* — Barry L. Davison; Davis Wright Tremaine LLP

(57) ABSTRACT

Provided are methods for forming a reactive S-nitroso thioacid (NTA), comprising nitrosation of a thioacid with a nitrosation reagent. Also provided are methods for: acylating a nucleophile including selective acylation with a high degree of selectivity toward amines over hydroxyls; amide or peptide bond formation; forming a dipeptide or polypeptide; and peptide coupling/ligation, comprising use of thioacid and amine starting materials, wherein the reactions are mediated by very reactive S-nitroso thioacid (NTA) intermediates enabling extremely fast reactions under mild conditions, providing for broad applications.

31 Claims, 1 Drawing Sheet

(56) References Cited

OTHER PUBLICATIONS

Shangguan, et al. (2003). "The Reaction of Thio Acids with Azides: A New Mechanism and New Synthetic Applications." *Journal of the American Chemical Society*. vol. 125, pp. 7754-7755.

Sheehan, John. C. And Johnson, David a. "The Synthesis and Reactions of N-ACYL Thiol Amino Acids." *Journal of the American Chemical Society*. vol. 74, pp. 4726-4727.

Szacilowski, Konrad and Stasicka, Zofia. (2000). "S-Nitrosothiols: Materials, Reactivity and Mechanisms." *Progress in Reaction Kinetics and Mechanism*. vol. 26, pp. 1-58.

Wang, Hua and Xian, Ming. (2008). "Fast Reductive Ligation of S-Nitrosothiols." *Angewandte Chemie International Edition*. vol. 47, pp. 6598-6601.

Wang, Hua, et al. (2009). "Facile Formation of Dehydroalanine From SNitrosocysteines." *Journal of the American Chemical Society*. vol. 131, pp. 13238-13239.

Wang, Peng George, et al. (2002). "Nitric Oxide Donors: Chemical Activities and Biological Applications." *Chemical Reviews*. vol. 102, No. 4, pp. 1091-1134.

Wang, Ping and Danishefsky, Samuel J. (2010). "A Promising General Solution to the Problem of Ligating Peptides and Glycopeptides." *Journal of the American Chemical Society*. vol. 132, pp. 17045-17051. (Author Manuscript version submitted herein).

Williams, D. Lyn. H. (1996). The mechanism of nitric oxide formation from S-nitrosothiols (thionitrites). *Chemical Communications*. Issue 10, pp. 1085-1091.

Williams, D. Lyn. H. (1999). "The Chemistry of S-Nitrosothiols." *Accounts of Chemical Research*. vol. 32, No. 10, pp. 869-876.

Zhang, Jiming, et al. (2009). "An Unexpected Bis-ligation of S-Nitrosothiols." *Journal of the American Chemical Society*. vol. 131, pp. 3854-3855.

Zhang, Jiming, et al. (2010). "Reductive Ligation Mediated One-Step Disulfide Formation of S-Nitrosothiols." *Organic Letters*. vol. 12, No. 18, pp. 4208-4211.

\* cited by examiner

FACILE AMIDE FORMATION VIA S-NITROSO THIOACID INTERMEDIATES

CROSS-REFERENCE TO RELATED APPLICATIONS

This application claims the benefit of priority to U.S. Provisional Patent Application No. 61/436,533 filed 26 Jan. 2011 and entitled "FACILE AMIDE FORMATION VIA S-NITROSO THIOACID INTERMEDIATES," which is incorporated herein by reference in its entirety.

FEDERAL FUNDING ACKNOWLEDGEMENT

This invention was made with government support under Grant/Contract No R01GM088226 awarded by the National Institute of Health, and CAREER award No. 0844931 from the National Science Foundation (NSF). The government has certain rights in the invention.

FIELD OF THE INVENTION

Particular aspects relate generally to amide or peptide bond formation, and more particularly to amide or peptide bond formation using thioacid and amine starting materials, wherein the reaction is mediated by very reactive S-nitroso thioacid (NTA) intermediates enabling extremely fast reactions under mild conditions, providing for broad applications including but not limited to amide bond formation, peptide coupling/ligation, and selective acylation with a high degree of selectivity toward amines over hydroxyls.

BACKGROUND

Amide or peptide bond formation is an active area in organic chemistry due to the importance of these reactions in biology and drug discovery. A number of new strategies for the construction of amide bonds have been discovered in the past decade.[1] In particular, thioacid or thioester derivatives are attractive starting materials. Recent studies have revealed some unique reactivity of these sulfur-based compounds and demonstrated some advantages of them compared to carboxylic acid derivatives in amide and peptide bond forming sequences.[2] The present applicants, in recent efforts to develop new methods for the detection of S-nitrosothiols, have discovered a series of new reactions of S-nitroso compounds.[3] As appreciated in the art, S-nitrosothiols are unstable moieties, and their chemistry, especially synthetically useful reactions, have not been well studied.[4] S-nitroso thioacids (NTA) type molecules have never been clearly identified, although such compounds may be involved in some thiyl radical formation process.[5]

SUMMARY OF ASPECTS OF THE INVENTION

Particular aspects provide S-nitroso thioacid (NTA) intermediates by subjecting thioacids to nitrosation (Scheme 1), to yield the corresponding NTA.

Exemplary Scheme 1: NTA Coupling

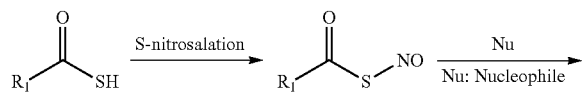

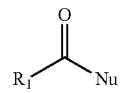

According to additional aspects, this sulfur-oxidation process activates thioacids and leads to a facile acylation with nucleophiles (e.g., including but not limited to primary and/or secondary amines).

Exemplary Scheme 2: Nitrosolation with organonitrite and nucleophillic amine

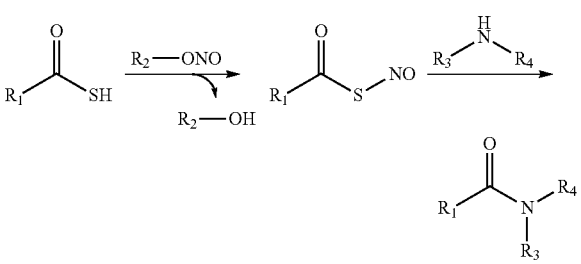

According to further aspects, the S-nitroso thioacid (NTA) intermediates are of broad general utility, including but not limited to amide bond formation, peptide coupling/ligation, and selective acylation with a high degree of selectivity toward amines over hydroxyls. In particular aspects, this thioacid activation via oxidation provides an effective and selective route to amide bond formation. In particular embodiments, the methods have substantial utility for peptide coupling/ligation reactions, and for polypeptide and protein synthesis.

In particular aspects, a new thioacid activation strategy via S-nitrosation is described herein. NTA, while unstable species, can rapidly and very effectively react with amines (both primary and secondary) under very mild conditions to form amides. The only reagent needed in this reaction is nitrosation reagents, e.g., HCl/NaNO$_2$ or organonitrites like amyl nitrite, which are relatively cheap and readily available from commercial sources. As disclosed herein, many amino acid side-chain functionalities such as hydroxyl (e.g., for serine, threonine, or tyrosine), carboxyl (e.g., aspartic acid, glutamic acid), and indole (for tryptophan) do not interfere with the reaction. Therefore, the disclosed NTA-mediated reaction is of a particular utility in protein syntheses because it substantially reduces or eliminates the need to use protecting groups on the amino acid residues bearing carboxylic acids or alcohols. This method can further be used in solid-support (e.g., resins) implementations (without side-chain protection) for modular peptide synthesis.

In particular aspects, the nitrosation agent comprises a nitrosonium salt, including for example but not limited to NOBF$_4$ and/or NOClO$_4$.

Moreover, according to further aspects, the side-chain protection-free capability enables native ligation for large peptide synthesis or protein synthesis; that is, in particular ligation embodiments, this method can be used to selectively couple polypeptide fragments to yield large synthetic biomolecules. Native chemical ligation methods are described, for example, in PCT/EP2006/005815, published as WO 2006/133962 A1, incorporated by reference herein in its entirety.

As demonstrated in Applicants' studies herein, aqueous buffers did not affect the reaction. According to particular aspects, therefore, NTA-mediated coupling can be carried out in aqueous buffer systems, which are particularly useful for handling and synthesis of larger polypeptides and/or proteins.

The methods disclosed herein, therefore, can be carried out in either aqueous, organic or aqueous/organic mixtures, and the nature of the solvent and resulting solution does not interfere with the underlying chemistry (see, e.g., table 3 below). In preferred embodiments, the solution is an aqueous solution. Depending on the hydrophobic or hydrophilic nature of the reagents, however, aqueous/organic or even organic solutions may be utilized.

DETAILED DESCRIPTION

Figures 1A, 1B, 1C:
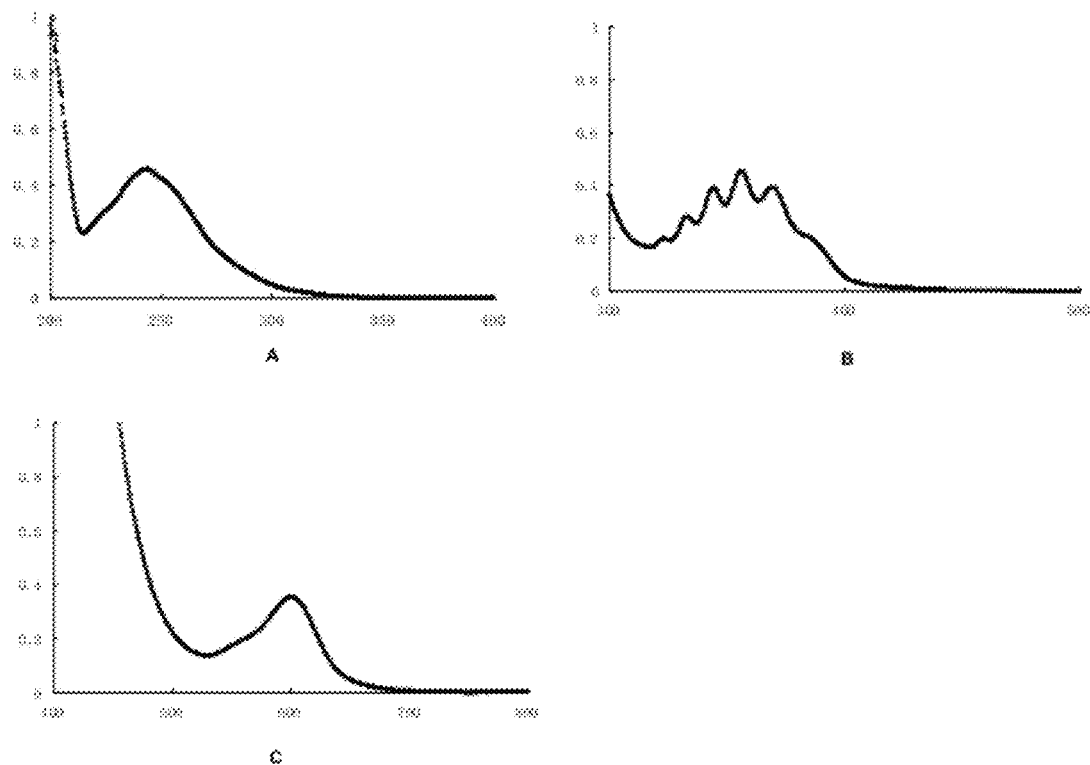
FIGS. 1A, B and C show, according to Example 1 herein, UV spectra of S-nitroso thiobenzoic acid 2 in $CH_3CN$.

Particular aspects relate generally to amide or peptide bond formation, and more particularly to amide or peptide bond formation using thioacid and amine starting materials, wherein the reaction is mediated by very reactive S-nitroso thioacid (NTA) intermediates enabling extremely fast reactions under mild conditions, providing for broad applications including by not limited to amide bond formation, peptide coupling/ligation, and selective acylation with a high degree of selectivity toward amines over hydroxyls.

Exemplary scheme 2 provides a generalized overview of the methods as described herein applied to and nucleophillic amines. In the preferred embodiment $R_1$, comprises an amino acid or polypeptide (less the carboxylic acid on the c-terminus). $R_3$ and $R_4$ are independently selected from H, an amino acid (less the NH) or a polypeptide (less the N-terminus. The amino acid (or those contained in a polypeptide) may be naturally occurring or synthetic. $R_2$ comprises an organic group (e.g., methyl, ethyl, propyl. butyl, pentyl, cyclopentyl, hexyl, cyclohexyl, amyl, aryl, and branched derivatives thereof that may contain one or more functional groups (e.g., —OH, —CO2H, —CO, —O—).

Example 1 herein describes and demonstrates that the S-nitroso thioacid (NTA) intermediate formed by treating thiobenzoic acid 2 with organonitrite (RONO; e.g., amyl nitrite) or $HCl/NaNO_2$ in organic solution at room temperature (rt) or at 0° C. can be trapped in situ with a nucleophile such as a nucleophilic amine, whereas, alcohols (such as benzyl alcohol, phenol, and N-hydroxysuccinimide) did not react with NTA to form esters (see Scheme 2 of Example 1). According to particular aspects, therefore, the presently disclosed methods provide for selective acylation with a high degree of selectivity toward amines over hydroxyls.

Example 2 herein describes optimization of the conditions for the disclosed NTA-mediated coupling between thioacids and amines. The best mode procedure for reacting thiobenzoic acid 1 and α-methyl benzylamine was to mix the thioacid (1.0 equivalent) and the amine (1.1 equivalents) at 0° C., followed by dropwise addition of amyl nitrite (2.0 equivalents) into the solution. The formation of the desired amide product was observed immediately and in high yields.

As shown in Scheme 3 (entries 1-4) of this Example, this reaction worked nicely in a number of common solvents including THF, DCM, DMF, and $CH_3CN$. Water seemed to have little effect on the coupling, as the reaction gave similar results in aqueous buffer-containing systems (entries 5 and 6). This process proved to be a very fast process as in all the solvents the reaction completed in minutes at 0° C.

Example 3 herein shows control experiments that were carried out by applicants to prove that the acylation was mediated by NTA (see Scheme 4-A of Example 3 for details). Additionally, Applicants attempted to capture the unstable NTA intermediates using the reductive ligation,[3a] which is a specific reaction of SNO groups. After several attempts, we were able to obtain the desired ligation product 6 using substrate 1a (Scheme 4-B). Although the yield of 6 was only 23%, the formation of this sulfenamide product strongly supported the presence of NTA intermediate in the reaction.

Example 4 herein shows data obtained with series of thioacids and amines that were employed under the optimized conditions to demonstrate the broad generality/applicability of applicants' NTA mediated reaction methods. The reaction proved to be effective with both exemplary primary and exemplary secondary amines (entries 1-8). Amino acids derivatives also proved to be good substrates in the reaction and the corresponding dipeptide products were obtained in good yields (entries 9-13). As shown in entry 10, free hydroxyl group did not interfere with the reaction. In all the cases, the reaction was able to complete in 10 minutes at 0° C.

Particular exemplary aspects, therefore, provide a novel amide bond formation strategy based on use of simple thioacids and amines. The disclosed process, as shown by the data presented herein, is mediated by very reactive S-nitroso thioacid (NTA) intermediates enabling extremely fast reactions under mild conditions, providing for broad applications including by not limited to amide bond formation, peptide coupling/ligation, and selective acylation with a high degree of selectivity toward amines over hydroxyls. This work supports the concept that thioacids can become highly effective acyl donors upon oxidative activation.[2b,2i,6]

According to particular aspects, given the fast reaction rate and very mild reaction conditions, this method has substantial and broad utility for selective acylation, peptide synthesis and protein synthesis.

Particular aspects provide a method for forming a reactive S-nitroso thioacid (NTA), comprising nitrosation of a thioacid with a nitrosation reagent (e.g., at least one selected from the group consisting of an organonitrite (RONO), HCl/$NaNO_2$, and a nitrosonium salt) in solution. In certain embodiments, the thioacid is selected from a compound having formula I:

(I)

wherein $R_1$ is selected from essentially any appropriate moiety or group, including but not limited to an amino acid or polypeptide (less the carboxylic acid on the c-terminus), or any moiety or group shown in the exemplary thioacid structures of Table 1 or of the exemplary working examples herein, or as described herein. In certain aspects, the solution comprises an aqueous solution. In particular embodiments, the solution comprises an aqueous-organic mixture. In certain aspects, the solution comprises an organic solution. In particular embodiments, the organonitrite comprises amyl nitrite.

Additional aspects provide a method for acylating a nucleophile, comprising: nitrosation of a thioacid with a nitrosation reagent (e.g., at least one selected from the group consisting of an organonitrite (RONO), HCl/$NaNO_2$, and a nitrosonium salt) in solution to form a reactive S-nitroso thioacid (NTA) intermediate; and contacting the NTA intermediate with a nucleophile to provide for acylation of the nucleophile. In particular aspects, the thioacid is selected from a compound having formula I:

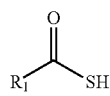

(I)

wherein $R_1$ is selected from essentially any appropriate moiety or group, including but not limited to an amino acid or polypeptide (less the carboxylic acid on the c-terminus), or any moiety or group shown in the exemplary thioacid structures of Table 1 or of the exemplary working examples herein, or as described herein. In certain embodiments, the nucleophile is selected from a primary or secondary amine. In certain aspects, the solution comprises an aqueous solution. In particular embodiments, the solution comprises an aqueous-organic mixture. In certain aspects, the solution comprises an organic solution. In particular embodiments, the organonitrite comprises amyl nitrite.

Additional aspects provide a method for forming an amide bond, comprising: nitrosation of a thioacid with a nitrosation reagent (e.g., at least one selected from the group consisting of an organonitrite (RONO), HCl/NaNO$_2$, and a nitrosonium salt) in solution to form a reactive S-nitroso thioacid (NTA) intermediate; and contacting the NTA intermediate with an amine to provide for forming an amide bond. In particular aspects, the thioacid is selected from a compound having formula I:

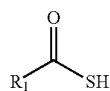

(I)

wherein $R_1$ is selected from essentially any appropriate moiety or group, including but not limited to an amino acid or polypeptide (less the carboxylic acid on the c-terminus), or any moiety or group shown in the exemplary thioacid structures of Table 1 or of the exemplary working examples herein, or as described herein. In certain embodiments, the amine is selected from a primary or secondary amine. In certain aspects, the solution comprises an aqueous solution. In particular embodiments, the solution comprises an aqueous-organic mixture. In certain aspects, the solution comprises an organic solution. In particular embodiments, the organonitrite comprises amyl nitrite.

Yet additional aspects provide a method for forming an dipeptide or polypeptide, comprising: nitrosation of a thioacid with a nitrosation reagent (e.g., at least one selected from the group consisting of an organonitrite (RONO), HCl/NaNO$_2$, and a nitrosonium salt) in solution to form a reactive S-nitroso thioacid (NTA) intermediate; and contacting the NTA intermediate with an amine to provide for forming a dipeptide or polypeptide. In particular aspects, the thioacid is selected from a compound having formula I:

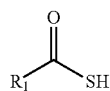

(I)

wherein $R_1$ is selected from essentially any appropriate moiety or group, including but not limited to an amino acid or polypeptide (less the carboxylic acid on the c-terminus), or any moiety or group shown in the exemplary thioacid structures of Table 1 or of the exemplary working examples herein, or as described herein. In certain embodiments, the nucleophile is selected from a primary or secondary amine. In certain aspects, the solution comprises an aqueous solution. In particular embodiments, the solution comprises an aqueous-organic mixture. In certain aspects, the solution comprises an organic solution. In particular embodiments, the organonitrite comprises amyl nitrite.

Further aspects provide a method for ligating two polypeptides to form a larger polypeptide, comprising: nitrosation of a thioacid derivative of a first polypeptide with a nitrosation reagent (e.g., at least one selected from the group consisting of an organonitrite (RONO), HCl/NaNO$_2$, and a nitrosonium salt) in solution to form a reactive S-nitroso thioacid (NTA) intermediate; and contacting the NTA intermediate with an amine group of a second polypeptide to provide for forming a larger, ligated polypeptide. In particular aspects, the first and the second polypeptides comprise contiguous amino acid subregions of a desired larger polypeptide.

According to particular preferred aspects, this sulfur-oxidation process activates thioacids and leads to a facile acylation with nucleophiles (e.g., including but not limited to primary and/or secondary amines).

Exemplary Scheme 2: Nitrosolation with organonitrite and nucleophillic amine

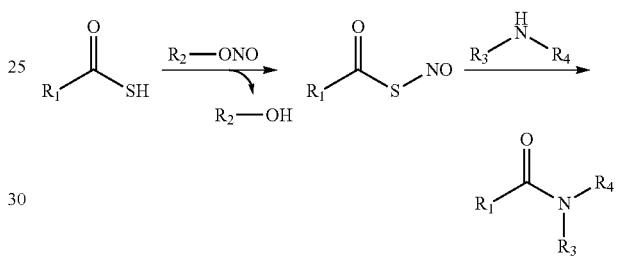

wherein $R_1$ is selected from essentially any appropriate moiety or group, including but not limited to an amino acid or polypeptide (less the carboxylic acid on the c-terminus), or any moiety or group shown in the exemplary thioacid structures of Table 1 or of the exemplary working examples herein; and/or wherein, for example, $R_1$, $R_3$, $R_4$ are the same or different and independently selected from an amino acid side chain moiety or derivative thereof, the remainder of the molecule, a linker and a solid support, and stereoisomers thereof.

In particular aspects, $R_1$, $R_3$, $R_4$ are independently selected from the group consisting of amino$C_{2-5}$alkyl, guanidine $C_{2-5}$alkyl, $C_{1-4}$alkylguanidino$C_{2-5}$alkyl, di$C_{1-4}$alkylguanidino-$C_{2-5}$alkyl, amidino$C_{2-5}$alkyl, $C_{1-4}$alkylamidino $C_{2-5}$alkyl, di$C_{1-4}$alkylamidino$C_{2-5}$alkyl, $C_{1-3}$alkoxy, Phenyl, substituted phenyl (where the substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), benzyl, substituted benzyl (where the substituents on the benzyl are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-3}$alkyl, nitro, carboxy, cyano, sulfuryl or hydroxyl), naphthyl, substituted naphthyl (where the substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), bisphenyl methyl, substituted bis-phenyl methyl (where the substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), pyridyl, substituted pyridyl, (where the substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), pyridyl$C_{1-4}$alkyl, substituted pyridyl$C_{1-4}$alkyl (where the pyridine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), pyrimidyl$C_{1-4}$alkyl, substituted pyrimidyl$C_{1-4}$alkyl (where the pyrimidine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), triazin-2-yl-$C_{1-4}$alkyl, substituted triazin-2-yl-$C_{1-4}$alkyl (where the triazine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), imidazo$C_{1-4}$alkyl, substituted imidazol $C_{1-4}$alkyl (where the imidazole substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl or hydroxyl), imidazolinylCalkyl, N-amidinopiperazinyl-N—$C_{0-4}$alkyl, hydroxy$C_{2-5}$alkyl, $C_{1-5}$alkylamino$C_{2-5}$alkyl, hydroxy$C_{2-5}$alkyl, $C_{1-5}$alkylamino$C_{2-5}$alkyl, $C_{1-5}$dialkylamino $C_{2-5}$alkyl, N-amidinopiperidinyl$C_{1-4}$alkyl and 4-aminocyclohexyl$C_{0-2}$alkyl.

As used herein, the term "remainder of the compound" means any moiety, agent, compound, support, molecule, linker, amino acid, peptide or protein covalently attached to the structure at $R_1$, $R_3$, and/or $R_4$ positions. This term also includes amino acid side chain moieties and derivatives thereof.

As used herein, the term "amino acid side chain moiety" represents any amino acid side chain moiety present in naturally occurring proteins including (but not limited to) the naturally occurring amino acid side chain moieties identified in Table 1. Other naturally occurring amino acid side chain moieties of this invention include (but are not limited to) the side chain moieties of 3,5-dibromotyrosine, 3,5-diiodotyrosine, hydroxylysine, γ-carboxyglutamate, phosphotyrosine and phosphoserine. In addition, glycosylated amino acid side chains may also be used in the practice of this invention, including (but not limited to) glycosylated threonine, serine and asparagine. In particular aspects, the amino acid side chains as defined herein are linked to the carbonyl carbon of the thioacid via an alpha carbon atom, which itself may be substituted (e.g., —$NH_2$, or as described herein for substituted amino acid side chains).

TABLE 1

Amino Acid Side Chain Moieties

| Amino Acid Side Chain Moiety | Amino Acid |
|---|---|
| —H | Glycine |
| —$CH_3$ | Alanine |
| —$CH(CH_3)_2$ | Valine |
| —$CH_2CH(CH_3)_2$ | Leucine |
| —$CH(CH_3)CH_2CH_3$ | Isoleucine |
| —$(CH_2)_4NH_3^+$ | Lysine |
| —$(CH_2)_3NHC(NH_2)NH_2^+$ | Arginine |
| | Histidine |

TABLE 1-continued

Amino Acid Side Chain Moieties

| Amino Acid Side Chain Moiety | Amino Acid |
|---|---|
| —$CH_2COO^-$ | Aspartic acid |
| —$CH_2CH_2COO^-$ | Glutamic acid |
| —$CH_2CONH_2$ | Asparagine |
| —$CH_2CH_2CONH_2$ | Glutamine |
| | Phenylalanine |
| | Tyrosine |
| | Tryptophan |
| —$CH_2SH$ | Cysteine |
| —$CH_2CH_2SCH_3$ | Methionine |
| —$CH_2OH$ | Serine |
| —$CH(OH)CH_3$ | Threonine |
| | Proline |
| | Hydroxyproline |

In addition to naturally occurring amino acid side chain moieties, the amino acid side chain moieties of the present invention also include various derivatives thereof. As used herein, a "derivative" of an amino acid side chain moiety includes modifications and/or variations to naturally occurring amino acid side chain moieties. For example, the amino acid side chain moieties of alanine, valine, leucine, isoleucine and pheylalanine may generally be classified as lower chain alkyl, aryl, or arylalkyl moieties. Derivatives of amino acid side chain moieties include other straight chain or branched, cyclic or noncyclic, substitutes or unsubstituted, saturated or unsaturated lower chain alkyl, aryl or arylalkyl moieties.

As used herein, "lower chain alkyl moieties" contain from 1-12 carbon atoms, "lower chain aryl moieties" contain from 6-12 carbon atoms and "lower chain aralkyl moieties" contain from 7-12 carbon atoms. Thus, in one embodiment, the amino acid side chain derivative is selected from a $C_{1-12}$ alkyl, a $C_{6-12}$ aryl and a $C_{7-12}$ arylalkyl, and in a more preferred embodiment, from a $C_{1-7}$ alkyl, a $C_{6-10}$ aryl and a $C_{7-11}$ arylalkyl.

Amino side chain derivatives of this invention further include substituted derivatives of lower chain alkyl, aryl, and arylalkyl moieties, wherein the substituent is selected from (but are not limited to) one or more of the following chemical moieties: —OH, —OR, —COOH, —COOR, —$CONH_2$, —$NH_2$, —NHR, —NRR, —SH, —SR, —$SO_2R$, —$SO_2H$, —SOR and halogen (including F, Cl, Br and I), wherein each occurrence of R is independently selected from straight chain or branched, cyclic or noncyclic, substituted or unsubstituted, saturated or unsaturated lower chain alkyl, aryl, and aralkyl moieties. Moreover, cyclic lower chain alkyl, aryl and arylalkyl moieties of this invention include naphthalene, as well as heterocyclic compounds such as thiophene, pyrrole, furan, imidazole, oxazole, thiazole, pyrazole, 3-pyrroline, pyrrolidine, pyridine, pyrimidine, purine, quinoline, isoquinoline and carbazole. Amino acid side chain derivatives further include heteroalkyl derivatives of the alkyl portion of the lower chain alkyl and aralkyl moieties, including (but not limited to) alkyl and aralkyl phosphonates and silanes.

In a further embodiment, and in addition to being an amino acid side chain moiety or derivative thereof (or the remainder of the compound in the case of $R_1$, $R_3$, and/or $R_4$ may be a linker facilitating the linkage of the compound to another moiety or compound. For example, the compounds of this invention may be linked to one or more known compounds, such as biotin, for use in diagnostic or screening assay. Furthermore, $R_1$, $R_3$, and/or $R_4$ may be a linker joining the compound to a solid support (such as a support used in solid phase peptide synthesis) or alternatively, may be the support itself.

In this embodiment, linkage to another moiety or compound, or to a solid support, is preferable at the $R_1$ position.

EXAMPLE 1

Formation of NTA Intermediates, and the Reactions of NTA Intermediates were Tested The preparation of NTA was tested in this example. An exemplary reaction scheme using thiobenzoic acid 1 is shown in Scheme 2 below. Compound 1 (thiobenzoic acid) was treated with organonitrite (RONO; e.g., amyl nitrite) or HCl/NaNO$_2$ in organic solutions at room temperature (rt) or at 0° C.

Figure 2:
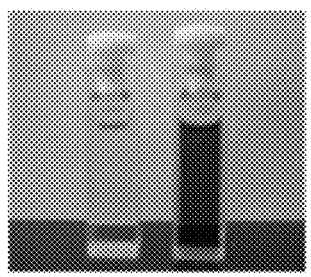
FIG. 2 shows, in gray scale, the color of S-nitroso thiobenzoic acid 1. The cuvette at the left of the figure (thiobenzoic acid, 83 mM) shows, in gray scale, the characteristic color (yellow) of thiobenzoic acid, whereas the cuvette on the right of the figure (thiobenzoic acid (83 mM)+iso-amyl nitrite (167 mM) shows, in gray scale, a color (deep green), which is the characteristic color of tertiary S-nitrosothiols.

The resulted species, presumably NTA 2, showed a deep green color, which is the characteristic color of tertiary S-nitrosothiols (FIG. 2).

The UV spectra of NTA 2 are shown in FIGS. 1A, 1B and 1C.

Specifically, FIGS. 1A, 1B and 1C show, according to particular aspects, UV-vis spectra of S-nitroso thiobenzoic acid 2 in CH$_3$CN at three different wavelengths: A) 213-268 nm region (39 µM, $\epsilon=1.14\times10^4$ M$^{-1}$ cm$^{-1}$), attributed to the it $\pi \rightarrow \pi^*$ transition[1]; B) 315-385 nm region (460 µM, $\epsilon=9.67\times 10^2$ M$^{-1}$ cm$^{-1}$), attributed to the $n_0 \rightarrow \pi^*$ transition[2]; and C) 531-633 nm region (27 mM, $\epsilon=13.2$ M$^{-1}$ cm$^{-1}$), attributed to the forbidden $n_N \rightarrow \pi^*$ transition (this band determines the compound's color)[3]. These three UV-vis absorption bands of compound 2 are very similar to the characteristic UV-vis bands of S-nitrosothiols.[1-3]

The NTA 2 appeared to be unstable as the green color readily faded when we attempted to isolate compound 2. The final isolated product was disulfide 3, which is the expected decomposition product from S-nitrosothiols. Although NTA 2 was unstable, applicants tested the idea to trap NTA in situ with some nucleophiles. Amines proved to be excellent substrates, and the formation of amide bonds were achieved in a very effective way (see TABLE 1 below). However, alcohols (such as benzyl alcohol, phenol, and N-hydroxysuccinimide) did not react with NTA to form esters.

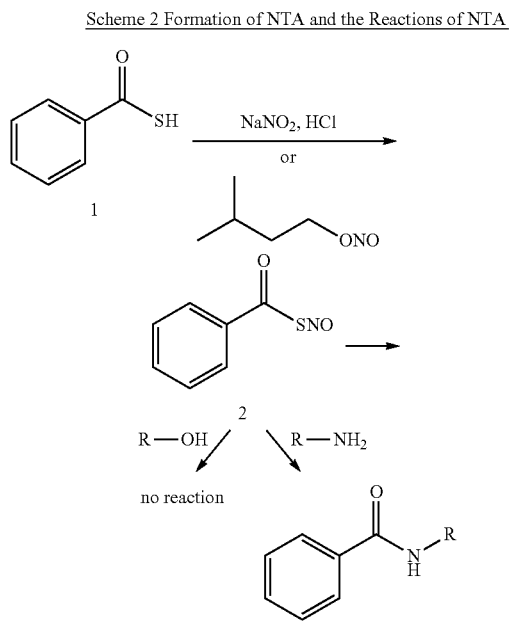

Scheme 2 Formation of NTA and the Reactions of NTA

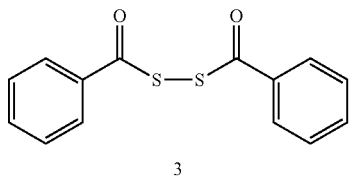

3

EXAMPLE 2

The Conditions for NTA Mediated Coupling Between Thioacids and Amines were Optimized In this Example, the conditions for this NTA mediated coupling between thioacids and amines were optimized. The best mode procedure was to mix the thioacid (1.0 eq) and the amine (1.1 eq) at 0° C., followed by dropwise addition of amyl nitrite (2.0 eq) into the solution. The formation of the desired amide product was observed immediately and in high yields, as monitored by thin layer chromatography (TLC).

As shown in Scheme 3 (entries 1-4) below, this reaction worked nicely in a number of common solvents including THF, DCM, DMF, and CH$_3$CN. Water seemed to have little effect on the coupling, as the reaction gave similar results in aqueous buffer-containing systems (entries 5 and 6). This process proved to be a very fast process as in all the solvents the reaction completed in minutes at 0° C.

Scheme 3 Solvent Effects of NTA Mediated Amide Formation

| entry | solvent | reaction time | yield of 4a |
|---|---|---|---|
| 1 | THF | 5 min | 96% |
| 2 | DCM | 10 min | 82% |
| 3 | DMF | 10 min | 75% |
| 4 | CH$_3$CN | 5 min | 94% |
| 5 | THF/PBS buffer (3/1) | 10 min | 95% |
| 6 | DMF/PBS buffer (1/1) | 20 min | 71% |

EXAMPLE 3

Control Experiments Showed that the Acylation was Mediated by NTA Intermediates In this Example, to prove the reaction was indeed involving NTA, several control experiments (Scheme 4) were carried out. The reaction between thioacid 1 and α-methyl-benzylamine only led to the formation of amide 4a in trace amount at room temperature, even when the amine was used in large access (10 eq). A previous report by Liu and Orgel, 1997, also suggested that thioacids should not directly react with amines to form amides.[2i] We also attempted to capture the unstable NTA intermediates using the reductive ligation,[3a] which is a specific reaction of SNO groups. After several attempts, we were able to obtain the desired ligation product 6 using substrate 1a (Scheme 4-B). Although the yield of 6 was only 23%, the formation of this sulfenamide product strongly supported the presence of NTA intermediate in the reaction.

Scheme 4: Control Experiments

A)

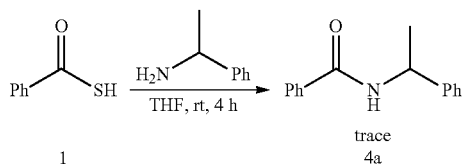

B)

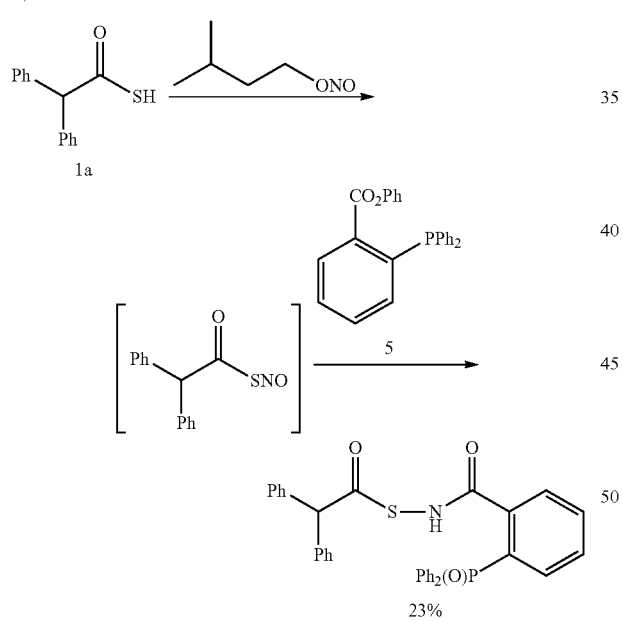

Reductive ligation reaction to produce Compound 6.

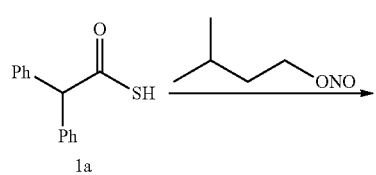

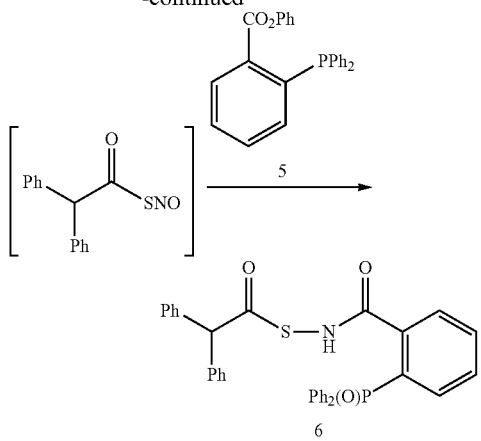

To a solution of 1a (36 mg, 0.16 mmol) in THF/CH$_3$CN/H$_2$O (1.5 mL/1.5 mL/1.0 mL) was added amyl nitrite (64 µL, 0.47 mmol) at 0° C. The resulting green solution was stirred for ~5 min at 0° C. Then, phosphine 5 (114 mg, 0.30 mmol, in 1.0 mL THF) was added into the solution. The reaction was stirred for additional 5 min. The reaction mixture was diluted with ethyl acetate (15 mL) and washed with an aqueous solution of 5% H$_2$O$_2$ (3 mL), saturated NaHSO$_3$ (3 mL) and brine. The organic layer was dried over Na$_2$SO$_4$ and concentrated. The crude product was purified by flash column chromatography (MeOH:DCM/1:200) to give 6 in 23% yield. $^1$H NMR (600 MHz, CDCl$_3$) δ 9.92 (s, 1H), 8.07-8.06 (m, 1H), 7.66-7.61 (m, 5H), 7.57-7.55 (m, 2H), 7.47-7.44 (m, 5H), 7.30-7.26 (m, 10H), 7.16-7.13 (m, 1H); $^{13}$C NMR (150 MHz, CDCl$_3$) 196.9, 168.2, 139.1(d), 137.2, 133.4(d), 132.7(d), 132.6(d), 132.5(d), 132.4(d), 131.9(d), 131.8, 130.7, 130.0, 129.0, 128.9, 128.8(d), 128.7(d), 128.6, 127.6, 61.3; $^{31}$P NMR (121 Hz, CDCl$_3$) 36.6. IR (thin film) cm$^{-1}$ 3061, 2923, 2855, 1715, 1682, 1589, 1495, 1437, 1252, 1168, 1120, 725, 695; HRMS m/z, 548.1449 [M+H]; calcd for C$_{33}$H$_{27}$NO$_3$PS, 548.1449.

EXAMPLE 4

A Series of Thioacids and Amines were Employed Under Optimized Conditions to Demonstrate the Broad Generality/Applicability of Applicants' NTA Mediated Reaction Methods The results of the above Examples indicate that NTA acts as an effective activating group to facilitate amide formation. In this Example, to test the broad generality of this reaction, a series of exemplary thioacids and exemplary amines were employed under optimized conditions (see Table 2 below). The reaction proved to be highly effective with both exemplary primary and exemplary secondary amines (entries 1-8). Amino acids derivatives also proved to be good substrates in the reaction and the corresponding dipeptide products were obtained in good yields (entries 9-13). As shown in entry 10, free hydroxyl group did not interfere with the reaction. In all the cases, the reaction was complete within 10 minutes at 0° C.

TABLE 2

NTA Mediated Amide Coupling

R-C(O)-SH + R¹-NH-R² → (isoamyl nitrite, THF, 0 °C) → R-C(O)-NR¹R²

| entry | thioacid | amine | product/yield |
|---|---|---|---|
| 1 | PhC(O)SH (1) | BnNH₂ | Ph-C(O)-NH-Bn, 4b (100%) |
| 2 | | t-BuNH₂ | Ph-C(O)-NH-t-Bu, 4c (97%) |
| 3 | | pyrrolidine | Ph-C(O)-N(pyrrolidine), 4d (80%) |
| 4 | | Bn₂NH | Ph-C(O)-NBn₂, 4e (88%) |
| 5 | | H₂N-CH₂-CO₂Me | Ph-C(O)-NH-CH₂-CO₂Me, 4f (89%) |
| 6 | | H₂N-CH(CH₂Ph)-CO₂Me | Ph-C(O)-NH-CH(CH₂Ph)-CO₂Me, 4g (77%) |
| 7 | CbzHN-CH₂-C(O)SH (1b) | BnNH₂ | CbzHN-CH₂-C(O)-NH-Bn, 4h (86%) |
| 8 | | pyrrolidine | CbzHN-CH₂-C(O)-N(pyrrolidine), 4i (87%) |

TABLE 2-continued

NTA Mediated Amide Coupling

| entry | thioacid | amine | product/yield |
|---|---|---|---|
| 9 | | H₂N-CH(CH₂Ph)-CO₂Me | CbzHN-CH₂-C(O)-NH-CH(CH₂Ph)-CO₂Me  4j (89%) |
| 10 | | H₂N-CH(CH₂OH)-CO₂Me | CbzHN-CH₂-C(O)-NH-CH(CH₂OH)-CO₂Me  4k (81%) |
| 11 | FmocHN-CH(CH₃)-C(O)SH  1c | H₂N-CH(CH₂Ph)-CO₂Me | FmocHN-CH(CH₃)-C(O)-NH-CH(CH₂OH)-CO₂Me  4l (86%) |
| 12 | | Pyrrolidine-CO₂Bn (HN) | FmocHN-CH(CH₃)-C(O)-N(pyrrolidine-CO₂Bn)  4m (80%) |
| 13 | BocHN-CH(CH₂Ph)-C(O)SH  1d | H₂N-CH₂-CO₂Me | BocHN-CH(CH₂Ph)-C(O)-NH-CH₂-CO₂Me  4n (87%) |

EXAMPLE 5

Materials and Methods

Materials and Methods. All solvents were reagent grade. Tetrahydrofuran (THF) was freshly distilled from sodium/benzophenone under argon. Reactions were magnetically stirred and monitored by thin layer chromatography (TLC) with 0.25 mm pre-coated silica gel plates. Flash chromatography was performed with silica gel 60 (particle size 0.040-0.062 mm). Yields refer to chromatographically and spectroscopically pure compounds, unless otherwise stated. Proton and carbon-13 NMR spectra were recorded on a 300 MHz spectrometer. Chemical shifts are reported relative to chloroform ($\delta$ 7.26) for $^1$H NMR and chloroform ($\delta$ 77.0) for $^{13}$C NMR. Absorption spectra were recorded on a Lambda 20 UV/Vis spectrophotometer using 1 cm quartz cells.

Thiobenzoic acid 1 was purchased from Aldrich. Other thioacids (i.e. 1a-1d) were prepared from known procedures.[4,5]

Experimental Procedures and Compound Characterization Data. FIGS. 1A, 1B and 1C show, according to particular aspects, UV-vis spectra of S-nitroso thiobenzoic acid 2 in CH₃CN at three different wavelengths: A) 213-268 nm region (39 μM, $\epsilon$=1.14×10⁴ M⁻¹ cm⁻¹), attributed to the $\pi \rightarrow \pi^*$ transition[1]; B) 315-385 nm region (460 μM, $\epsilon$=9.67×10² M⁻¹ cm⁻¹), attributed to the $n_O \rightarrow \pi^*$ transition[2]; and C) 531-633 nm region (27 mM, $\epsilon$=13.2 M⁻¹ cm⁻¹), attributed to the forbidden $n_N \rightarrow \pi^*$ transition (this band determines the compound's color)[3]. These three UV-vis absorption bands of 2 are very similar to the characteristic UV-vis bands of S-nitrosothiols.[1-3]

Color of S-Nitroso Thiobenzoic Acid 2. FIG. 2 compares the color of thiobenzoic acid (1, yellow) with that of S-nitroso thiobenzoic acid (2, dark green) The cuvette on the left contained thiobenzoic acid (83 mM in CH$_3$CN), which was yellow, whereas the cuvette on the right contained thiobenzoic acid (83 mM in CH$_3$CN) plus iso-amyl nitrite (167 mM), which was a dark green color.

EXAMPLE 6

General Procedure of NTA Mediated Amide Formation

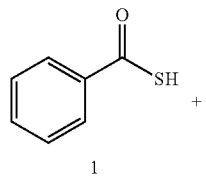

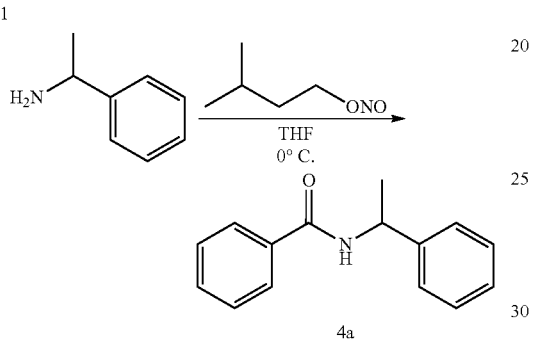

To a stirred solution of thioacid 1 (69 mg, 0.5 mmol) and α-methyl benzylamine (67 mg, 0.55 mmol) in THF (5 mL) at 0° C. in darkness, amyl nitrite (117 mg, 1 mmol) was slowly added (dropwise). The reaction was stirred at 0° C. for 5 minutes, and the reaction mixture then diluted with CH$_2$Cl$_2$ (20 mL) and washed with water and brine. The organic layer was dried with anhydrous Na$_2$SO$_4$. The solvent was then removed under reduced pressure. The crude product was purified by flash column chromatography (hexane/ethyl acetate, 10/1) to afford the desired product 4a (108 mg, 96%).

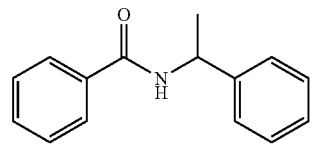

Yield 96%; white solid, m.p. 120-121° C.; $^1$H NMR (300 MHz, CDCl$_3$): δ 7.66 (2H, d, J=7.8 Hz), 7.37-7.12 (8H, m), 6.70 (1H, d, J=7.2 Hz), 5.21 (1H, dt, J=7.2 Hz), 1.46 (3H, d, J=6.9 Hz); $^{13}$C NMR (75 MHz, CDCl$_3$): δ 167.0, 143.5, 134.8, 131.7, 128.9, 128.7, 127.6, 127.3, 126.5, 49.5, 22.0; IR (thin film) cm$^{-1}$ 3341, 3067, 2974, 1633, 1579, 1530, 1491, 1449, 1322, 1276, 1210, 1148, 1029, 872, 802, 762, 698; MS m/z 248.1 [M+Na$^+$].

EXAMPLE 7

Preparation of Compound 4B

Compound 4b. Preparation: see general procedures under Example 6 for reaction conditions.

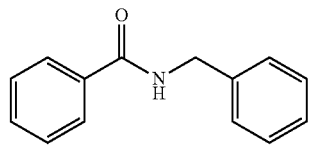

Yield 100%; white solid, m.p. 101-102° C.; $^1$H NMR (300 MHz, CDCl$_3$): δ 7.80 (2H, d, J=6.9 Hz), 7.46 (1H, tt, J$_1$=7.5 Hz, J$_2$=1.5 Hz), 7.37-7.23 (8H, m), 4.55 (2H, d, J=6.0 Hz); $^{13}$C NMR (75 MHz, CDCl$_3$): δ 167.9, 138.7, 134.6, 131.7, 128.9, 128.7, 128.0, 127.6, 127.4, 44.2; IR (thin film) cm$^{-1}$ 3323, 3060, 2930, 2856, 1643, 1604, 1578, 1547, 1490, 1453, 1419, 1362, 1313, 1260, 1158, 1080, 1058, 1029, 990, 928, 805, 794, 728, 696, 666; MS m/z 212.1 [M+Na$^+$].

EXAMPLE 8

Preparation of Compound 4c

Compound 4c. Preparation: see general procedures under Example 6 for reaction conditions.

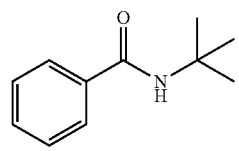

Yield 97%; white solid, m.p. 131-132° C.; $^1$H NMR (300 MHz, CDCl$_3$): δ 7.68 (2H, d, J=7.5 Hz), 7.41-7.29 (3H, m), 6.14 (1H, s), 1.42 (9H, s); $^{13}$C NMR (75 MHz, CDCl$_3$): δ 167.2, 136.1, 131.2, 128.6, 127.0, 51.8, 29.0; IR (thin film) cm$^{-1}$ 3317, 2965, 1632, 1578, 1534, 1492, 1450, 1364, 1312, 1218, 1078, 936, 877, 720, 694; MS m/z 178.0 [M+H$^+$].

EXAMPLE 9

Preparation of Compound 4d

Compound 4d. Preparation: see general procedures under Example 6 for reaction conditions.

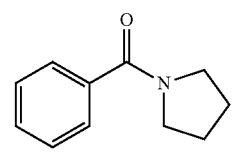

Yield 80%; colorless oil; $^1$H NMR (300 MHz, CDCl$_3$): δ 7.48-7.44 (2H, m), 7.36-7.31 (3H, m), 3.59 (2H, t, J=6.9 Hz), 3.36 (2H, t, J=6.6 Hz), 1.95-1.76 (4H, m); $^{13}$C NMR (75 MHz, CDCl$_3$): δ 169.9, 137.4, 129.9, 128.4, 127.3, 49.8, 46.3, 26.6, 24.7; IR (thin film) cm$^{-1}$ 2971, 2877, 1626, 1575, 1447, 1422, 719, 700, 658; MS m/z 198.1 [M+Na$^+$].

EXAMPLE 10

Preparation of Compound 4e

Compound 4e. Preparation: see general procedures under Example 6 for reaction conditions.

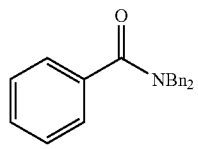

Yield 88%; white solid, m.p. 96-97° C.; $^1$H NMR (300 MHz, CDCl$_3$): δ 7.55-7.52 (2H, m), 7.41-7.32 (11H, m), 7.18-7.16 (2H, m), 4.74 (2H, s), 4.43 (2H, s); $^{13}$C NMR (75 MHz, CDCl$_3$): δ 172.5, 137.2, 136.7, 136.7, 136.4, 129.9, 129.1, 129.0, 128.8, 128.7, 127.9, 127.8, 127.3, 127.0, 51.8, 47.1; IR (thin film) cm$^{-1}$ 3028, 2924, 1632, 1602, 1495, 1450, 1422, 1365, 1307, 1259, 1204, 1142, 1077, 1028, 992, 731, 698; MS m/z 302.2 [M+H]$^+$.

EXAMPLE 11

Preparation of Compound 4f

Compound 4f. Preparation: see general procedures under Example 6 for reaction conditions.

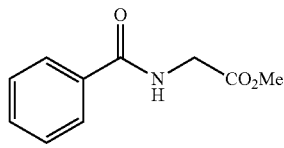

Yield 89%; colorless oil; $^1$H NMR (300 MHz, CDCl$_3$): δ 7.80 (2H, dt, $J_1$=6.6 Hz, $J_2$=1.5 Hz), 7.49 (1H, tt, $J_1$=7.5 Hz, $J_2$=1.5 Hz), 7.42-7.37 (2H, m), 6.95 (1H, s), 4.21 (2H, d, J=5.1 Hz), 3.76 (3H, s); $^{13}$C NMR (75 MHz, CDCl$_3$): δ 170.8, 167.9, 133.8, 132.0, 128.8, 127.3, 52.7, 41.9; IR (thin film) cm$^{-1}$ 3331, 3063, 2953, 1754, 1650, 1536, 1491, 1439, 1408, 1371, 1314, 1211, 1183, 1080, 1006, 976, 719, 693; HRMS m/z 194.0811 [M+H]$^+$; calcd for $C_{10}H_{12}NO_3$: 194.0812.

EXAMPLE 12

Preparation of Compound 4g

Compound 4g. Preparation: see general procedures under Example 6 for reaction conditions.

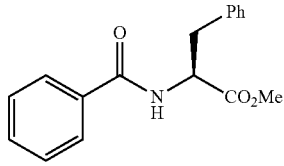

Yield 77%; colorless oil $^1$H NMR (300 MHz, CDCl$_3$): δ 7.72 (2H, dt, $J_1$=6.6 Hz, $J_2$=1.5 Hz), 7.50 (1H, tt, $J_1$=7.5 Hz, $J_2$=1.5 Hz), 7.44-7.38 (2H, m), 7.33-7.25 (3H, m), 7.15-7.12 (2H, m), 6.65 (1H, d, J=7.2 Hz), 5.12-5.06 (1H, m), 3.76 (3H, s), 3.33-3.19 (2H, m); $^{13}$C NMR (75 MHz, CDCl$_3$): δ 172.2, 167.1, 136.1, 134.1, 132.0, 129.6, 128.9, 127.4, 127.2, 53.8, 52.7, 38.1; IR (thin film) cm$^{-1}$ 3319, 3030, 2952, 1745, 1643, 1603, 1580, 1537, 1490, 1437, 1360, 1217, 1098, 1028, 912, 701; HRMS m/z 284.1294 [M+H]$^+$; calcd for $C_{17}H_{18}NO_3$: 284.1281.

EXAMPLE 13

Preparation of Compound 4h

Compound 4h. Preparation: see general procedures under Example 6 for reaction conditions.

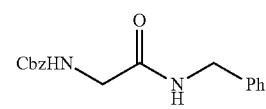

Yield 86%; white solid, m.p. 107-108° C.; $^1$H NMR (300 MHz, CDCl$_3$): δ 7.35-7.21 (10H, m), 6.78 (1H, s), 5.75 (1H, s), 5.03 (2H, s), 4.38 (2H, d, J=5.7 Hz), 3.84 (2H, d, J=5.4 Hz); $^{13}$C NMR (75 MHz, CDCl$_3$): δ 169.3, 156.9, 138.0, 136.3, 128.9, 128.8, 128.7, 128.5, 128.3, 127.9, 127.8, 67.4, 44.8, 43.7; IR (thin film) cm$^{-1}$ 3321, 3062, 2925, 1693, 1666, 1548, 1537, 1454, 1427, 1360, 1287, 1246, 1164, 1068, 1006, 736, 696; HRMS m/z 299.1384 [M+H]$^+$; calcd for $C_{17}H_{19}N_2O_3$: 299.1390.

EXAMPLE 14

Preparation of Compound 4i

Compound 4i. Preparation: see general procedures under Example 6 for reaction conditions.

Yield 87%; white solid, m.p. 62-63° C.; $^1$H NMR (300 MHz, CDCl$_3$): δ 7.37-7.30 (5H, m), 5.79-5.78 (1H, m), 5.12 (2H, s), 3.94 (2H, d, J=4.2 Hz), 3.49 (2H, t, J=6.6 Hz), 3.37 (2H, t, J=6.6 Hz), 2.03-1.94 (2H, m), 1.92-1.82 (2H, m); $^{13}$C NMR (75 MHz, CDCl$_3$): δ 166.5, 156.5, 136.7, 128.7, 128.3, 128.3, 67.1, 46.2, 45.6, 43.7, 26.2, 24.4; IR (thin film) cm$^{-1}$ 3539, 3487, 3279, 2957, 1696, 1628, 1549, 1452, 1412, 1333, 1266, 1173, 1052, 981, 763, 704; HRMS m/z 263.1379 [M+H]$^+$; calcd for $C_{14}H_{19}N_2O_3$: 263.1390.

EXAMPLE 15

Preparation of Compound 4j

Compound 4j. Preparation: see general procedures under Example 6 for reaction conditions.

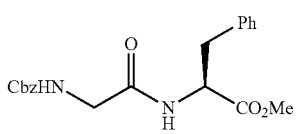

4j

Yield 89%; colorless oil $^1$H NMR (300 MHz, CDCl$_3$): δ 7.33-7.32 (5H, m), 7.28-7.18 (3H, m), 7.08 (2H, d, J=6.0 Hz), 6.85 (1H, d, J=7.8 Hz), 5.73 (1H, t, J=5.4 Hz), 5.09 (2H, s), 4.87 (1H, dd, J$_1$=13.8 Hz, J$_2$=6.0 Hz), 3.83-3.81 (2H, m), 3.67 (3H, s), 3.14-3.00 (2H, m); $^{13}$C NMR (75 MHz, CDCl$_3$): δ 172.1, 169.1, 156.8, 136.4, 135.9, 129.5, 128.8, 128.8, 128.4, 128.3, 127.4, 67.3, 53.4, 52.6, 44.5, 38.1, 31.8, 22.9, 14.4; IR (thin film) cm$^{-1}$ 3319, 3031, 2952, 1728, 1674, 1530, 1454, 1351, 1216, 1178, 1118, 1049, 988, 912, 737, 700; HRMS m/z 371.1600 [M+H]$^+$; calcd for C$_{20}$H$_{23}$N$_2$O$_5$: 371.1601.

EXAMPLE 16

Preparation of Compound 4k

Compound 4k. Preparation: see general procedures under Example 6 for reaction conditions.

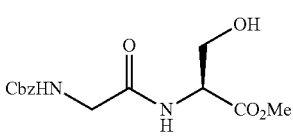

4k

Yield 81%; white solid, m.p. 90-91° C.; $^1$H NMR (300 MHz, CDCl$_3$): δ 7.37-7.31 (5H, m), 7.29-7.28 (1H, m), 5.86 (1H, t, J=5.4 Hz), 5.09 (2H, s), 4.65-4.61 (1H, m), 3.97-3.82 (4H, m), 3.73 (3H, s), 3.62 (1H, t, J=4.8 Hz); $^{13}$C NMR (75 MHz, CDCl$_3$): δ 171.2, 169.9, 157.2, 136.3, 128.8, 128.5, 128.3, 67.5, 62.8, 54.9, 53.0, 44.5; IR (thin film) cm$^{-1}$ 3331, 2954, 1726, 1710, 1666, 1547, 1530, 1441, 1345, 1236, 1134, 1052, 738, 698; HRMS m/z 311.1233 [M+H]$^+$; calcd for C$_{14}$H$_{19}$N$_2$O$_6$: 311.1238.

EXAMPLE 17

Preparation of Compound 4l

Compound 4l. Preparation: see general procedures under Example 6 for reaction conditions.

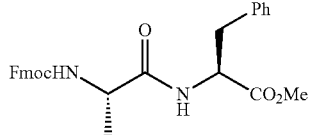

4l

Yield 86%; white solid, m.p. 157-158° C.; $^1$H NMR (300 MHz, CDCl$_3$): δ 7.77 (2H, d, J=7.5 Hz), 7.59 (2H, d, J=7.2 Hz), 7.41 (2H, t, J=7.2 Hz), 7.32 (2H, dt, J$_1$=7.2 Hz, J$_2$=1.2 Hz), 7.21 (3H, t, J=7.5 Hz), 7.07 (2H, t, J=3.6 Hz), 6.38 (1H, d, J=7.5 Hz), 5.28 (1H, d, J=6.9 Hz), 4.89-4.83 (1H, m), 4.44-4.31 (2H, m), 4.25-4.19 (2H, m), 3.72 (3H, s), 3.20-3.04 (2H, m), 1.36 (3H, d, J=6.9 Hz); $^{13}$C NMR (75 MHz, CDCl$_3$): δ 171.9, 171.8, 144.0, 141.5, 135.8, 129.4, 128.2, 128.0, 127.4, 127.3, 125.3, 125.3, 120.2, 67.4, 53.4, 52.7, 50.6, 47.3, 38.0; IR (thin film) cm$^{-1}$ 3303, 3063, 2951, 1742, 1711, 1661, 1530, 1450, 1252, 1215, 1118, 1080, 1046, 759, 740, 701; HRMS m/z 473.2071 [M+H]$^+$; calcd for C$_{28}$H$_{29}$N$_2$O$_5$: 473.2071.

EXAMPLE 18

Preparation of Compound 4m

Compound 4m. Preparation: see general procedures under Example 6 for reaction conditions.

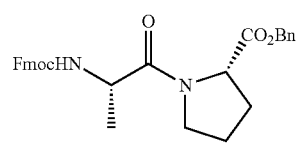

4m

Yield 80%; white solid, m.p. 49-50° C.; $^1$H NMR (300 MHz, CDCl$_3$): δ 7.76 (2H, d, J=7.5 Hz), 7.59 (2H, d, J=7.2 Hz), 7.42-7.28 (9H, m), 5.72 (1H, d, J=8.1 Hz), 5.22, 5.12 (2H, AB, J=12.3 Hz), 4.63-4.58 (1H, m), 4.56-4.48 (1H, m), 4.34 (2H, d, J=7.2 Hz), 4.21 (1H, t, J=7.2 Hz), 3.77-3.57 (2H, m), 2.27-2.19 (1H, m), 2.11-1.94 (3H, m), 1.36 (3H, d, J=6.9 Hz); $^{13}$C NMR (75 MHz, CDCl$_3$): δ 171.8, 171.5, 155.8, 144.1, 144.0, 141.5, 135.7, 128.8, 128.6, 128.4, 127.9, 127.3, 125.4, 120.2, 67.2, 59.1, 48.5, 47.3, 47.1, 29.2, 25.2, 18.6; IR (thin film) cm$^{-1}$ 3286, 3064, 2978, 2881, 1742, 1721, 1642, 1530, 1501, 1451, 1379, 1248, 1172, 1044, 910, 759, 739, 699; HRMS m/z 499.2230 [M+H]$^+$; calcd for C$_{30}$H$_{31}$N$_2$O$_5$: 499.2227.

EXAMPLE 19

Preparation of Compound 4n

Compound 4n. Preparation: see general procedures under Example 6 for reaction conditions.

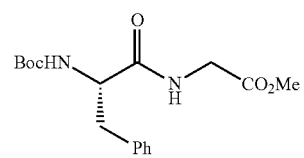

4n

Yield 87%; colorless oil; $^1$H NMR (300 MHz, CDCl$_3$): δ 7.29-7.18 (5H, m), 6.77 (1H, t, J=4.8 Hz), 5.23 (1H, d, J=5.1 Hz), 4.45 (1H, d, J=6.0 Hz), 4.05-3.88 (2H, m), 3.70 (3H, s), 3.12 (1H, dd, J$_1$=13.8 Hz, J$_2$=4.8 Hz), 3.03-2.96 (1H, m), 1.36 (9H, s); $^{13}$C NMR (75 MHz, CDCl$_3$): δ 172.0, 170.2, 155.7, 136.9, 129.5, 128.8, 127.1, 80.3, 55.8, 53.7, 52.5, 41.4, 38.6, 28.4; IR (thin film) cm$^{-1}$ 3314, 2978, 1754, 1665, 1530, 1501, 1440, 1367, 1250, 1211, 1170, 1022, 856, 700; HRMS m/z 337.1756 [M+H]$^+$; calcd for C$_{17}$H$_{25}$N$_2$O$_5$: 337.1758.

EXAMPLE 20

Preparation of Compound 4o

Compound 4o. Preparation: see general procedures under Example 6 for reaction conditions.

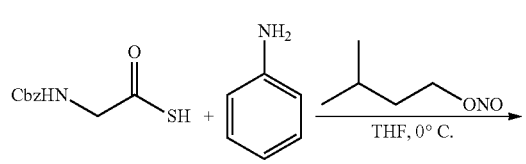
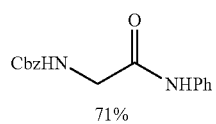
Product yield: 71%. $^1$H NMR (300 MHz, CDCl$_3$) δ 8.25 (s, 1H), 7.48 (d, J=7.8 Hz, 2H), 7.35-7.27 (m, 7H), 7.11 (t, J=7.2 Hz, 1H), 5.70 (s, 1H), 5.15 (s, 2H), 4.02 (d, J=5.1 Hz, 2H); $^{13}$C NMR (75 MHz, CDCl$_3$) 167.2, 156.9, 137.3, 135.9, 129.0, 128.6, 128.3, 128.1, 124.6, 120.0, 67.4, 45.5; IR (thin film) cm$^{-1}$ 3330.7, 1693.6, 1673.7, 1601.5, 1541.4, 1444.0, 1291.2, 1251.4, 1202.5, 1162.4, 1054.4, 738.1, 692.5; Mass (m/z), 285.0 [M+H].
EXAMPLES 21-24
Preparation of Compounds 4p-4-s
Preparation: See General Procedures Under Example 6 for Reaction Conditions
4p
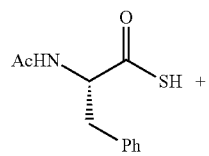
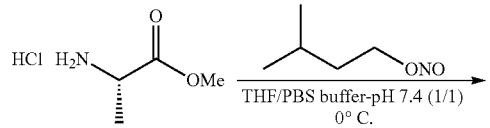
4q
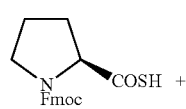
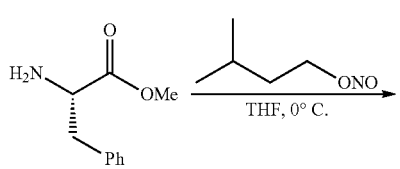
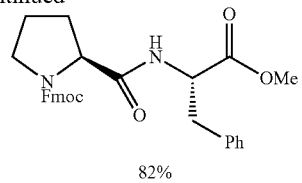
4r
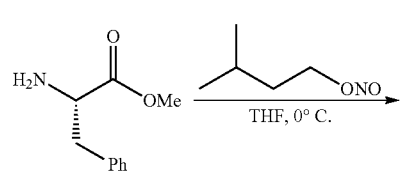
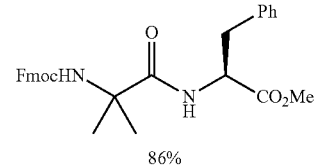
4s
EXAMPLE 25
Preparation of Compound 5a
Compound 5a. Preparation: see general procedures under Example 6 for reaction conditions.

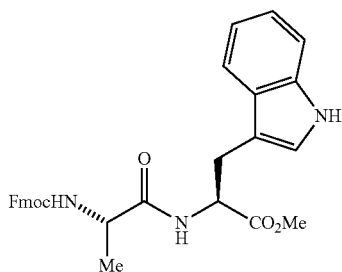

Yield 86%; white solid, m.p. 170-171° C.; $^1$H NMR (300 MHz, CDCl$_3$): δ 8.07 (1H, s), 7.78 (2H, d, J=7.5 Hz), 7.56 (2H, t, J=7.2 Hz), 7.52 (1H, d, J=9.9 Hz), 7.41 (2H, t, J=7.5 Hz), 7.15-7.04 (4H, m), 6.90 (2H, d, J=2.1 Hz), 6.67 (1H, d, J=7.2 Hz), 5.39 (1H, d, J=7.8 Hz), 4.92 (1H, m), 4.37-4.13 (4H, m), 3.65 (3H, s), 3.5 (2H, d, J=5.4 Hz), 1.32 (3H, d, J=6.9 Hz); $^{13}$C NMR (75 MHz, CDCl$_3$): δ 171.3, 156.1, 144.0, 141.5, 136.2, 128.0, 127.7, 127.3, 125.4, 125.3, 122.4, 120.3, 119.8, 118.6, 111.6, 109.8, 67.3, 53.1, 52.7, 50.6, 47.2, 31.8, 27.7, 22.9, 18.9, 14.4; IR (thin film) cm$^{-1}$ 3303, 3063, 2951, 1742, 1711, 1661, 1530, 1450, 1252, 1215, 1118, 1080, 1046, 759, 740, 701; MS m/z 534.3 [M+Na]$^+$; calcd for C$_{30}$H$_{29}$N$_3$NaO$_5$: 534.2.

EXAMPLE 26

Preparation of Compound 5b

Compound 5b. Preparation: see general procedures under Example 6 for reaction conditions.

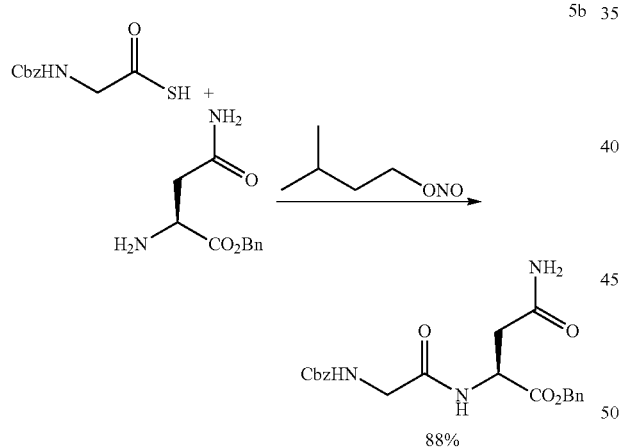

Data of the product: yield 88%; colorless oil; 138-139° C.; $^1$H NMR (300 MHz, CDCl$_3$): δ 7.70 (1H, d, J=7.8 Hz), 7.29-7.20 (10H, m), 6.10 (2H, d, J=16.2 Hz), 5.91 (1H, s), 5.12 (2H, s), 5.05 (2H, s), 4.80 (1H, s), 3.85 (2H, s), 2.86 (1H, d, J=15.0 Hz), 2.71 (1H, d, J=15.0 Hz); $^{13}$C NMR (75 MHz, CDCl$_3$): δ 172.8, 171.2, 169.8, 169.8, 156.9, 136.5, 135.5, 128.8, 128.6, 128.4, 128.3, 67.7, 67.3, 49.3, 44.3, 37.0; MS m/z 414.2 [M+H]$^+$; calcd for C$_{21}$H$_{24}$N$_3$O$_6$: 414.1.

EXAMPLE 27

Preparation of Compound 5c

Compound 5c. Preparation: see general procedures under Example 6 for reaction conditions.

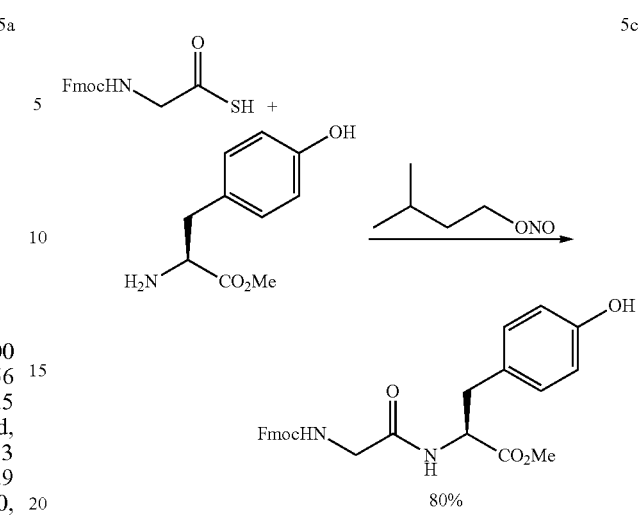

Data of the product: yield 80%; colorless oil; $^1$H NMR (300 MHz, CDCl$_3$): δ 7.70 (1H, d, J=7.8 Hz), 7.29-7.20 (10H, m), 6.10 (2H, d, J=16.2 Hz), 5.91 (1H, s), 5.12 (2H, s), 5.05 (2H, s), 4.80 (1H, s), 3.85 (2H, s), 2.86 (1H, d, J=15.0 Hz), 2.71 (1H, d, J=15.0 Hz); $^{13}$C NMR (75 MHz, CDCl$_3$): δ 172.2, 172.0, 170.8, 170.7, 157.8, 156.3, 144.1, 141.4, 130.1, 127.6, 127.2, 127.0, 125.1, 119.8, 115.1, 67.0, 54.3, 54.2, 51.5, 43.5, 36.5, 36.5; MS m/z 475.2 [M+H]$^+$; calcd for C$_{27}$H$_{27}$N$_2$O$_6$: 475.2.

EXAMPLE 28

Preparation of Compound 5d

Compound 5d. Preparation: see general procedures under Example 6 for reaction conditions.

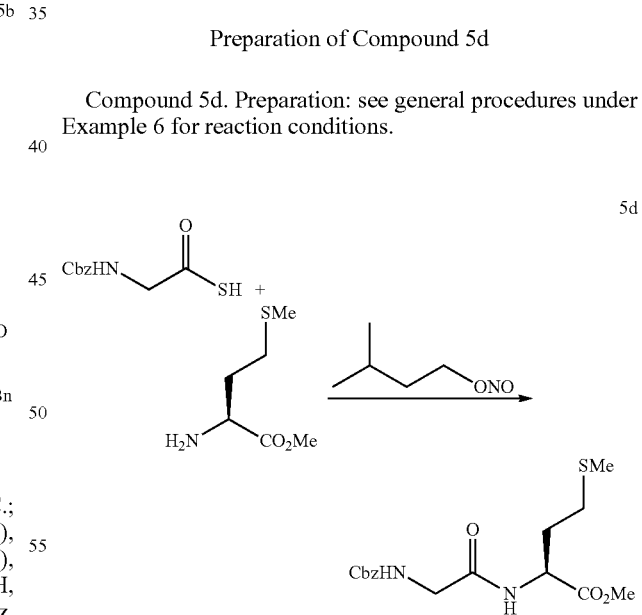

Data of the product: Yield 80%; colorless oil; $^1$H NMR (300 MHz, CDCl$_3$): δ 7.70 (1H, d, J=7.8 Hz), 7.29-7.20 (10H, m), 6.10 (2H, d, J=16.2 Hz), 5.91 (1H, s), 5.12 (2H, s), 5.05 (2H, s), 4.80 (1H, s), 3.85 (2H, s), 2.86 (1H, d, J=15.0 Hz), 2.71 (1H, d, J=15.0 Hz); $^{13}$C NMR (75 MHz, CDCl$_3$): δ 172.8, 171.2, 169.8, 169.8, 156.9, 136.5, 135.5, 128.8, 128.6, 128.4, 128.3, 67.7, 67.3, 49.3, 44.3, 37.0; MS m/z 475.2 [M+H]$^+$; calcd for C$_{27}$H$_{27}$N$_2$O$_6$: 475.2.

EXAMPLE 29

Preparation of Compound 5e

Compound 5e. Preparation: see general procedures under Example 6 for reaction conditions.

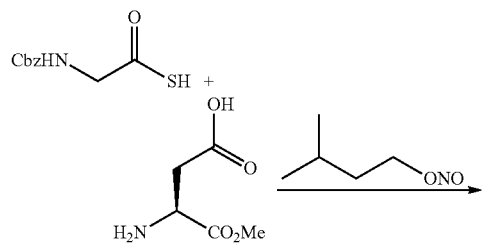

Data of the product: Yield 79%; colorless oil; $^1$H NMR (300 MHz, CDCl$_3$): δ 7.34-7.30 (10H, m), 5.72 (1H, s), 5.16 (2H, s), 5.08 (2H, s), 4.89 (1H, t, J=1.5 Hz), 3.99-3.92 (1H, m), 3.85 (1H, dd, J$_1$=8.4 Hz, J$_2$=2.4 Hz), 3.05 (1H, dd, J$_1$=8.7 Hz, J$_2$=2.1 Hz), 2.87 (1H, dd, J$_1$=8.7 Hz, J$_2$=1.8 Hz); $^{13}$C NMR (75 MHz, CDCl$_3$): δ 174.0, 170.6, 169.7, 157.1, 136.2, 135.2, 128.8, 128.8, 128.7, 128.5, 128.4, 128.3, 68.0, 67.6, 67.6, 48.9, 44.3, 36.1; MS m/z 415.1 [M+H]$^+$; calcd for C$_{21}$H$_{23}$N$_2$O$_7$: 415.2.

EXAMPLE 30

Preparation of Compound 5f

Compound 5f. Preparation: see general procedures under Example 6 for reaction conditions.

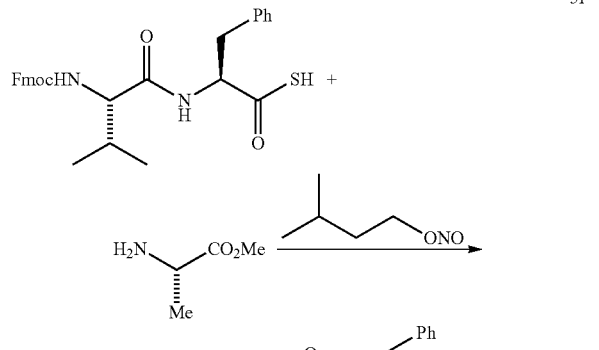

Data of the product: Yield 75%; white solid, m.p. 206-208° C.; $^1$H NMR (300 MHz, DMSO-d$_6$): δ 8.46 (1H, d, J=6.9 Hz), 8.00 (1H, d, J=8.4 Hz), 7.89 (2H, d, J=7.2 Hz), 7.20 (2H, q, J=3.6 Hz), 7.41 (2H, t, J=7.2 Hz), 7.32 (3H, t, J=7.5 Hz), 7.26-7.21 (4H, m), 7.14 (1H, d, J=5.4 Hz), 4.63-4.56 (1H, m), 4.33-4.21 (4H, m), 3.79 (1H, t, J=8.1 Hz), 3.60 (3H, s), 3.02 (1H, dd, J$_1$=13.8 Hz, J$_2$=4.2 Hz), 2.77 (1H, dd, J$_1$=13.8 Hz, J$_2$=9.6 Hz), 1.86 (1H, m), 1.27 (3H, d, J=7.2 Hz), 0.72 (6H, dd, J$_1$=12.0 Hz, J$_2$=6.9 Hz); $^{13}$C NMR (75 MHz, CDCl$_3$): δ 172.8, 171.0, 170.9, 155.9, 143.9, 143.7, 140.7, 137.5, 129.2, 127.9, 127.6, 127.0, 127.0, 126.2, 125.3, 120.1, 65.6, 60.4, 53.2, 51.8, 47.6, 46.7, 37.5, 30.4, 19.0, 18.2, 16.8; MS m/z 572.2 [M+H]$^+$; calcd for C$_{33}$H$_{38}$N$_3$O$_6$: 572.3.

EXAMPLE 31

Preparation of Compound 5g

Compound 5g. Preparation: see general procedures under Example 6 for reaction conditions.

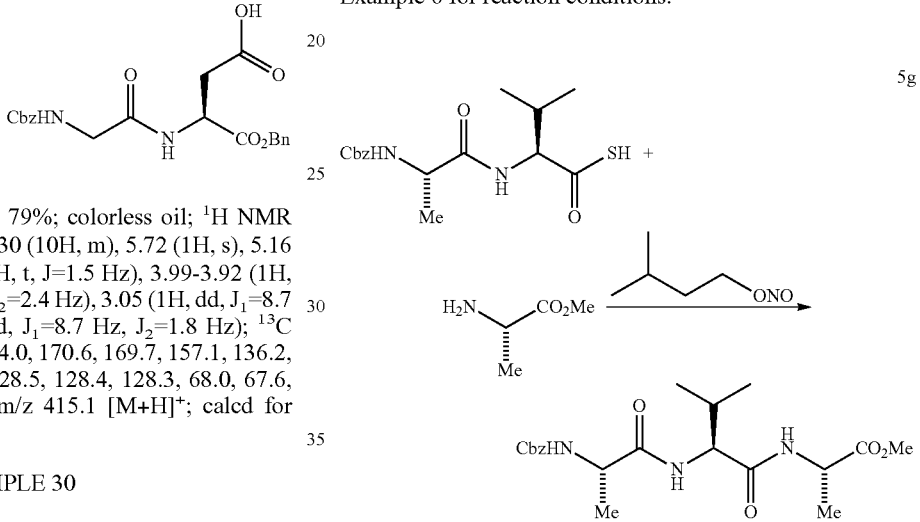

Data of the product: Yield 76%; white solid, m.p. 217-219° C.; $^1$H NMR (300 MHz, DMSO-d$_6$): δ 8.44 (1H, d, J=6.3 Hz), 7.66 (1H, d, J=9.0 Hz), 7.52 (1H, d, J=7.8 Hz), 7.34 (5H, q, J=3.6 Hz), 5.01 (2H, s), 4.27-4.18 (2H, m), 4.11 (1H, t, J=7.5 Hz), 3.60 (3H, s), 1.98-1.89 (1H, m), 1.27 (3H, d, J=7.2 Hz), 1.18 (3H, d, J=7.2 Hz), 0.85 (6H, dd, J$_1$=12.9 Hz, J$_2$=6.6 Hz); $^{13}$C NMR (75 MHz, CDCl$_3$): δ 172.9, 172.3, 170.8, 155.6, 137.0, 128.3, 127.8, 127.7, 65.3, 56.8, 51.7, 50.1, 47.6, 31.1, 19.0, 18.1, 17.9, 16.7; MS m/z 408.1 [M+H]$^+$; calcd for C$_{20}$H$_{30}$N$_3$O$_6$: 408.2.

REFERENCES

Incorporated Herein by Reference in their Entireties, and Particularly for their Respectively Chemical Synthetic and Structural Teachings

[1] Mason, J. B. *J. Chem. Soc. A.* 1969, 1587.

[2] Williams, D. L. H. *Chem. Commun.* 1996, 1085.

[3] Wang, P. G.; Xian, M.; Tang, X.; Wu, X.; Wen, Z.; Cai, T.; Janczuk, J. *J. Chem. Rev.* 2002, 102, 1091.

[4] Goldstein, A. S.; Gelb, M. H. *Tetrahedron Lett.* 2000, 41, 2797.

[5] Crich, D.; Sharma, I. *Angew. Chem. Int. Ed.* 2009, 48, 2355.

REFERENCES

Incorporated Herein by Reference in their Entireties, and Particularly for their Respectively Chemical Synthetic and Strurctural Teachings 1. For selected reviews, see (a) Bode, J. W. *Curr. Opin. Drug Discovery Dev.* 2006, 9, 765. (b) Han, S.; Kim, Y. *Tetrahedron* 2004, 60, 2447. (c) Nilsson, B. L.; Soellner, M. B.; Raines, R. T. *Annu. Rev. Biophys. Biomol. Struct.* 2005, 34, 91. (d) Kimmerlin, T.; Seebach, D. *J. Peptide Res.* 2005, 65, 229.
2. For selected examples, see (a) Bao, Y.; Li, X.; Danishefsky, S. J. *J. Am. Chem. Soc.* 2009, 131, 12924. (b) Wang, P.; Danishefsky, S. J. *J. Am. Chem. Soc.* 2010, 132, 17045. (c) Crich, D.; Sasaki, K. *Org. Lett.* 2009, 11, 3514. (d) Crich, D.; Sharma, I. *Angew. Chem. Int. Ed.* 2009, 48, 2355. (e) Crich, D.; Sharma, I. *Angew. Chem. Int. Ed.* 2009, 48, 7591. (f) Crich, D.; Sana, K.; Guo, S. *Org. Lett.* 2007, 9, 4423. (g) Dawson, P. E.; Muir, T. W.; Clark-Lewis, I.; Kent, S. B. H. *Science* 1994, 266, 776. (h) Dawson, P. E.; Churchill, Ghadiri, M. R.; Kent, S. B. H. *J. Am. Chem. Soc.* 1997, 119, 4325. (i) Liu, R.; Orgel, L. E. *Nature* 1997, 389, 52. (j) Shangguan, N.; Katukojvala, S.; Greenberg, R.; Williams, L. J. *J. Am. Chem. Soc.* 2003, 125, 7754.
3. (a) Wang, H.; Xian, M. *Angew Chem. Int. Ed.* 2008, 47, 6598. (b) Zhang, J.; Wang, H.; Xian, M. *J. Am. Chem. Soc.* 2009, 131, 3854. (c) Wang, H.; Xian, M. *J. Am. Chem. Soc.* 2009, 131, 13238. (d) Zhang, J.; Li, S.; Zhang, D.; Wang, H.; Whorton, A. R.; Xian, M. *Org. Lett.* 2010, 12, 4208. (d) Zhang, D.; Devarie-Baez, N. O.; Pan, J.; Wang, H.; Xian, M. *Org. Lett.* 2010, 12, 5674. (e) Devarie-Baez, N. O.; Xian, M. *Org. Lett.* 2010, 12, 752.
4. For selected reviews on S-nitrosothiols, see (a) Williams, D. L. H. *Acc. Chem. Res.* 1999, 32, 869. (b) Szacilowski, K.; Stasicka, Z. *Prog. React. Kinet. Mech.* 2000, 26, 1. (c) Al-Sadoni, H. H.; Ferro, A. *Current Med. Chem.* 2004, 11, 2679. (d) Wang, P. G.; Xian, M.; Tang, X.; Wu, X.; Wen, Z.; Cai, T.; Janczuk, A. J. *Chem. Rev.* 2002, 102, 1091.
5. Potapenko, D. I.; Bagryanskaya, E. G.; Tsentalovich, Y. P.; Reznikov, V. A.; Clanton, T. L.; Khramtsov, V. V. *J. Phys. Chem. B* 2004, 108, 9315.
6. Sheehan, J. C.; Johnson, D. A. *J. Am. Chem. Soc.* 1952, 74, 4726.

The invention claimed is:

1. A method for forming a reactive S-nitroso thioacid (NTA), comprising nitrosation of a thioacid with a nitrosation reagent in solution to form a reactive S-nitroso thioacid (NTA) intermediate wherein the thio moiety of the thioacid is nitrosated by the nitrosation reagent, wherein the thioacid is selected from a compound having formula I:

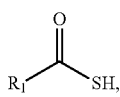

wherein $R_1$ is selected from any moiety or group.

2. The method of claim 1, wherein the solution comprises an aqueous solution.
3. The method of claim 1, wherein the solution comprises an aqueous-organic mixture.
4. The method of claim 1, wherein the solution comprises an organic solution.
5. The method of claim 1, wherein the nitrosation reagent comprises at least one reagent selected from the group consisting of an organonitrite (RONO), $HCl/NaNO_2$, and a nitrosonium salt.
6. The method of claim 5, wherein the organonitrite comprises amyl nitrite.
7. A method for acylating a nucleophile, comprising: nitrosation of a thioacid with a nitrosation reagent in solution to form a reactive S-nitroso thioacid (NTA) intermediate wherein the thio moiety of the thioacid is nitrosated by the nitrosation reagent; and contacting the NTA intermediate with a nucleophile to provide for acylation of the nucleophile, wherein the thioacid is selected from a compound having formula I:

wherein $R_1$ is selected from any moiety or group.

8. The method of claim 7, wherein the nucleophile is selected from a primary or secondary amine.
9. The method of claim 7, wherein the solution comprises an aqueous solution.
10. The method of claim 7, wherein the solution comprises an aqueous-organic mixture.
11. The method of claim 7, wherein the solution comprises an organic solution.
12. The method of claim 7, wherein the nitrosation reagent comprises at least one reagent selected from the group consisting of an organonitrite (RONO), $HCl/NaNO_2$, and a nitrosonium salt.
13. The method of claim 12, wherein the organonitrite comprises amyl nitrite.
14. A method for forming an amide bond, comprising: nitrosation of a thioacid with nitrosation reagent in solution to form a reactive S-nitroso thioacid (NTA) intermediate wherein the thio moiety of the thioacid is nitrosated by the nitrosation reagent; and contacting the NTA intermediate with an amine to provide for forming an amide bond, wherein the thioacid is selected from a compound having formula I:

wherein $R_1$ is selected from any moiety or group.

15. The method of claim 14, wherein the solution comprises an aqueous solution.
16. The method of claim 14, wherein the solution comprises an aqueous-organic mixture.
17. The method of claim 14, wherein the solution comprises an organic solution.
18. The method of claim 14, wherein the amine is selected from a primary and/or secondary amine.
19. The method of claim 14, wherein the nitrosation reagent comprises at least one reagent selected from the group consisting of an organonitrite (RONO), $HCl/NaNO_2$, and a nitrosonium salt.
20. The method of claim 19, wherein the organonitrite comprises amyl nitrite.

21. The method of claim 14, wherein contacting the NTA intermediate with an amine to provide for forming an amide bond comprises forming a dipeptide or polypeptide.

22. The method of claim 21, wherein the solution comprises an aqueous solution.

23. The method of claim 21, wherein the solution comprises an aqueous-organic mixture.

24. The method of claim 21, wherein the solution comprises an organic solution.

25. The method of claim 17, wherein the amine is selected from a primary and/or secondary amine.

26. The method of claim 17, wherein the nitrosation reagent comprises at least one reagent selected from the group consisting of an organonitrite (RONO), $HCl/NaNO_2$, and a nitrosonium salt.

27. The method of claim 26, wherein the organonitrite comprises amyl nitrite.

28. The method of claim 21, further comprising nitrosation of a thioacid derivative of the dipeptide or the polypeptide with a nitrosation reagent in solution to form a reactive S-nitroso thioacid (NTA) intermediate; and contacting the NTA intermediate with an amine group of a second polypeptide to provide for forming a larger, ligated polypeptide.

29. The method of claim 23, wherein the first and the second polypeptides comprise contiguous amino acid subregions of a desired larger polypeptide.

30. The method of claim 28, wherein the nitrosation reagent comprises at least one reagent selected from the group consisting of an organonitrite (RONO), $HCl/NaNO_2$, and a nitrosonium salt.

31. The method of claim 30, wherein the organonitrite comprises amyl nitrite.

* * * * *